Figure 1:
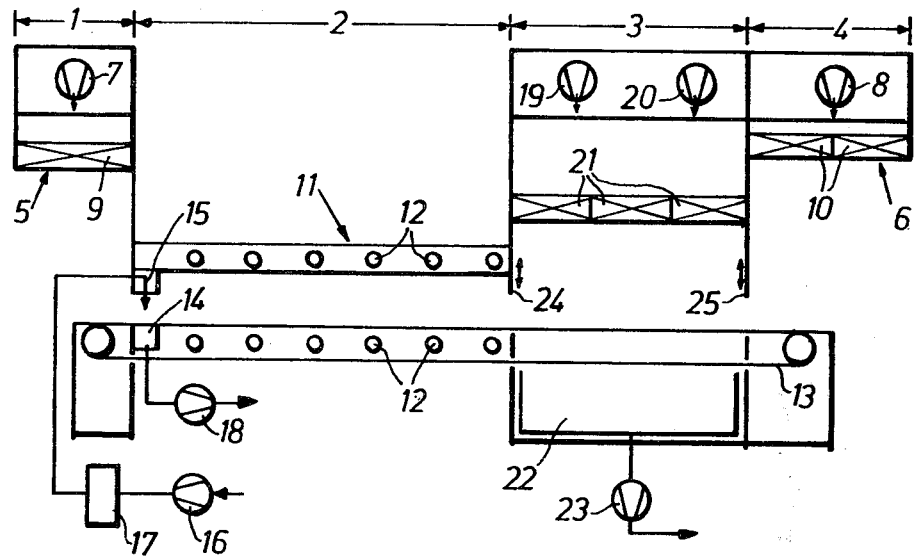

United States Patent [19]

Sirch et al.

[11] 4,140,479

[45] Feb. 20, 1979

[54] METHOD OF LOW PARTICLE STERILIZATION

[75] Inventors: Edgar Sirch, Leverkusen; Johann Franz; Günter Hoffmann, both of Monheim; Dirk-Torsten Krüger, Cologne; Paul-Günter Underberg, Bergisch-Gladbach, all of Fed. Rep. of Germany

[73] Assignee: Bayer Aktiengesellschaft, Leverkusen, Fed. Rep. of Germany

[21] Appl. No.: 808,584

[22] Filed: Jun. 21, 1977

[30] Foreign Application Priority Data

Jul. 13, 1976 [DE] Fed. Rep. of Germany ....... 2631352

[51] Int. Cl.² .............................................. F27B 9/12
[52] U.S. Cl. ..................................... 432/18; 432/145; 432/152; 422/304
[58] Field of Search ...................... 21/80; 432/18, 143, 432/144, 145, 152

[56] References Cited

U.S. PATENT DOCUMENTS

| 2,950,098 | 8/1960 | Ruff ....................................... 432/152 |
| 3,869,249 | 3/1975 | Frische ................................. 432/152 |

FOREIGN PATENT DOCUMENTS 2035822  1/1972  Fed. Rep. of Germany .............. 21/80

Primary Examiner—John J. Camby
Attorney, Agent, or Firm—Sprung, Felfe, Horn, Lynch & Kramer

[57] ABSTRACT

In a process for low particle sterilization of temperature resistant containers (glass bottles), the containers are continuously sterilized by radiant heat in a continuous heating furnace and then cooled by highly purified filtered air. One essential factor for obtaining the freedom from particles is the provision of a non-turbulent stream of highly purified air maintained in the continuous heating furnace in a direction parallel and opposite to the direction of movement of the containers.

9 Claims, 2 Drawing Figures

METHOD OF LOW PARTICLE STERILIZATION

The invention relates to a process and apparatus for the sterilization of heat resistant objects, such as glass bottles for parenteral drugs and other containers. The objects are continuously sterilized by radiant heat in a continuous heating furnace and then cooled by a blast of air. The cooling air used for this purpose is filtered in high power filters for suspended materials (HOSCH filters).

Glass containers used in the pharmaceutical industry for pharmaceutical preparations must be carefully sterilized. For this purpose, the containers are continuously passed through a radiant heat furnace on shelves or conveyor belts. Systematic measurements with particle counters have shown that in the absence of special measures a radiant furnace contains a high proportion of foreign particles, e.g. dust. Up to $10^4$ particles having an average diameter of more than 0.5 $\mu$m have been found in a liter of air. It is obvious that such a high concentration of foreign particles causes a high wastage rate in the end products of the process. The so-called laminar flow principle is therefore employed, in which streams of highly purified air of low turbulence are produced at the inlet and outlet end of the radiant furnace at right angles to the direction of movement of the containers (see, for example, German Auslegeschrift No. 1 936 865). Blowers are normally used to produce the air streams. The air is purified by high power filters for suspended particles immediately before it enters the furnace. These filters are known as HOSCH filters and are generally made of non-woven glass fibre webs. By means of this apparatus it is possible to reduce the particle count in the sterilization tunnel and in the adjacent inlet and outlet zones to a value conforming to the U.S. Federal Standard 209$b$. The particle counts measured in the whole region of the sterilization tunnel are of the order of 1 particle > 0.5 $\mu$m per liter of air. However, when the above mentioned sterilization apparatus with HOSCH filters are used at the inlet and outlet zones and within the sterilization zone, the purity of air is obtained at the expense of very high cost of apparatus.

It is an object of the present invention to provide a method of low particle sterilization which is more economical in its investment costs and energy consumption. The term "low particle" means that the particle count conforms at least to the requirements laid down in the U.S. Federal Standard 209$b$.

According to the invention, there is provided a process for the sterilization of heat resistant objects, comprising passing the objects through a continuous furnace in which they are sterilized by radiant heat through which furnace a low turbulence current of air having a low particle count (as herein defined) is passed parallel to the direction of movement of the objects and subsequently cooling the objects by means of air having a low particle count.

The low turbulence current is advantageously produced by a pressure gradient in the cooling zone following the exit from the furnace and the sterilization zone. In this way, a small portion of the cooling air which has been filtered through a HOSCH filter is branched off from the cooling zone and flows over the containers from the furnace outlet to the furnace inlet against the direction of movement of the containers. The pressure gradient is preferably adjusted so that the transverse current in the furnace has a velocity of from 0.2 to 0.7 m/sec.

A preferred embodiment of the invention is characterised in that the current of air is removed practically entirely by suction through an inlet gate at the entrance to the furnace.

According to the invention, there is also provided an apparatus for the sterilization of heat resistant objects, comprising a radiant heating tunnel furnace, a conveyor for continuously conveying the objects through the furnace, an inlet gate at the inlet end of the furnace comprising an air supply box connected to a blower, the height of which box above the conveyor is infinitely variably adjustable and an air withdrawal box below the conveyor connected to a blower, a cooling zone at the outlet from the furnace, at least one blower and a filter for suspended particles for supplying filtered air to the cooling zone, and at least one blower for withdrawing air from the cooling zone, all of said blowers being infinitely variably adjustable, so that the velocity of a current of air through the furnace is adjustable. Adjustable shutters may be provided between the furnace outlet and the cooling zone and between the cooling zone and the sterile zone. In addition, the air supply distributor of the inlet gate is infinitely variably adjustable in its height. The transverse current can therefore be regulated reproducibly with great accuracy.

The following advantages are achieved by the invention:

1. The standard of purity required by U.S. Federal Standard 209$b$ can be maintained throughout the entire furnace space. Measurements with a Royco particle counter manufactured by Bausch & Lomb showed that over long periods of time a particle concentration of about 1 particle > 0.5 $\mu$m per liter of air was maintained throughout the radiant furnace.
2. No HOSCH filters or blowers are required in the sterilization zone. This reduces the initial cost of the plant and the energy consumption.
3. The plant is easier to maintain because the sterilization zone is more easily accessible.
4. The excess pressure may safely be reduced, starting from the sterile zone to the outlet of the radiant furnace.
5. Another important advantage is that the HOSCH filters used need not be refractory since they are not fed with heated air but only with air from the surrounding atmosphere. It is therefore possible to use HOSCH filters made of organic fibres, which are preferable to glass fiber filters for medical and health reasons.
6. Glass fibre HOSCH filters also have the disadvantage that they require relatively narrow temperature tolerances to be observed in the high temperature region. If HOSCH filters are used within the sterilization zone and operated with hot air, complicated control devices are required to keep the temperature constant within the given narrow tolerances. In the process according to the invention, on the other hand, temperature control is not critical and need merely be maintained within a range of 300° to 320° C.
7. The high temperatures which can be reached in the sterilization zone ensure substantial depyrogenisation of the objects passing through it.

Figure 2:
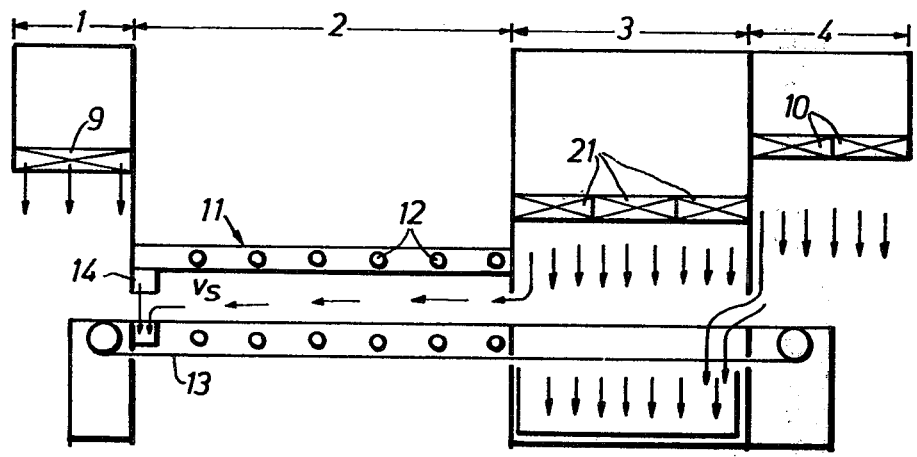

An example of the invention will now be described in more detail with reference to the drawings in which FIG. 1 is a schematic representation of the sterilization plant and FIG. 2 represents the sterilization plant with the directions of flow indicated in arrows.

The sterilization apparatus shown in FIG. 1 consists basically of four zones, the inlet zone 1, the sterilization zone 2, the cooling zone 3 and the outlet zone 4. The inlet zone 1 is at normal pressure. The outlet zone 4 is at an excess pressure of 124.6 μbar to conform to the adjacent sterile zone. The sterilization zone 2 is shielded off at the inlet and outlet by so-called laminar flow units 5 and 6. They consist of a blower 7 and 8, respectively, with a HOSCH filter 9 and 10 below it. These devices produce a curtain of HOSCH filtered air through which the containers pass at the inlet and outlet. The sterilization zone 2 proper consists of a radiant heating furnace 11 with heating rods 12.

The glass bottles which are to be sterilized are passed through the radiant furnace 11 on a conveyor belt 13. The furnace temperature is normally in the region of 300° to 320° C. The rate of transport is approximately 0.1 meter per minute. An inlet gate 14 is arranged at the furnace inlet. It is formed by two boxes 15 placed opposite each other and having air outlet apertures and suction apertures. The upper of the two boxes is capable of infinitely variable adjustment in height. Uniform distribution of air is achieved, for example, by using a perforated metal sheet for the undersurface of the air supply box or the top of the air discharge box. In addition to the air curtain at the inlet end 1, another air curtain of HOSCH filtered air is produced perpendicularly to the conveyor belt 13 in the region of the boxes 15. This curtain is produced by means of a blower 16. Since the inlet gate 14 already provides for uniform distribution of air, the HOSCH filter 17 may be arranged outside the radiant furnace 11 if the pipes carrying the filtered air do not contaminate it with particles.

The cooling zone 3 is adjacent to the outlet from the radiant furnace 11. The sterilized containers leaving the furnace are cooled to approximately room temperature in this region. The cooling zone 3 shown here is equipped with two blowers 19 and 20. These blowers are analogous to the laminar flow unit 5 and the air supply of the inlet gate 14 in producing a current of low turbulence perpendicular to the conveyor belt 13. HOSCH filters 21 are again provided between the blowers 19 and 20 and the conveyor belt 13. A reservoir 22 communicating with a blower 23 to suck off the cooling air is situated underneath the conveyor belt 13 in the region of the cooling zone 3. This reservoir 22 produces a uniform flow profile in the cooling zone 3. Adjustable shutters 24 and 25 are provided at the outlet of the furnace 11 and at the end of the cooling zone 3. They consist of substantially rectangular baffle plates adjustable in height and they partition off the sterilization zone 2 and cooling zone 3. The smallest permissible width of gap is the height of the containers to be sterilized.

All the HOSCH filters 9, 10, 17 and 21 are at room temperature. They may be made of non-woven webs of polycarbonate fibres which have a degree of filtration of more than 99.9% for dust particles above 0.5 μm.

FIG. 2 shows the conditions of flow in the sterilization zone 2, the cooling zone 3 and the outlet zone 4. The speeds of rotation of the blowers 16, 18, 19, 20 and 23 are infinitely adjustable. The exhaust air fan 23 in the cooling zone 3 is first adjusted so that the portion of air which is drawn into the cooling zone from the outlet zone 4 by the excess pressure in the sterile zone is removed by the fan 23. A portion of the air supplied by the blowers 19 and 20 is thereby caused to flow through the shutter 24 into the furnace 11 against the direction of movement of the containers and is removed by the exhaust air fan 18 at the furnace inlet. The output of the fan 18 must therefore be higher by this amount than that of the corresponding air supply blower 16 in order to remove the partial stream flowing through the furnace. Coarse adjustment of this partial stream is effected by adjusting the blowers 16, 18, 19, 20 and 23 while fine adjustment is obtained by means of the shutters 24 and 25. Optimum conditions of purity in the radiant furnace 11 are obtained when the rate of flow of the current of air is within the range of from 0.2 to 0.7 m/sec. Since this range is relatively wide, no complicated control devices are required to keep the flow velocity of the current of air constant.

The glass bottles to be sterilized are in many cases still wet when they enter the sterilization zone if they have previously been washed and rinsed. Due to the high temperatures in the furnace, they dry very rapidly in the first section of the furnace. The steam thereby produced is removed by the fan 18 which is for this reason referred to as the wet exhaust air fan. Sterilization takes place in the following sections of the furnace 11.

EXAMPLE

Glass bottles were sterilized under the following operating conditions:

| | |
|---|---|
| Pressure in outlet zone = Pressure in sterile zone | = 124.6 μbar |
| Pressure in cooling zone 3 above the conveyor belt | = 20 μbar |
| in the reservoir 22 | = −30 μbar |
| Pressure in radiant furnace 11 (middle) | = 5 μbar |
| Pressure at inlet to radiant furnace 11 | = 20 μbar. |

Under these pressure conditions, a transverse current flowing at a velocity of $v_s = 0.2$ m/sec is established in the radiant furnace.

What we claim is:

1. A process for the continuous sterilization of heat resistant objects comprising: continuously transporting the objects; sterilizing the objects by radiation heating in a sterilizing zone having an inlet end and an outlet end; providing a first air curtain of low particle count air at the inlet and perpendicular to the direction of transport to define an inlet zone through which the objects pass; cooling the heated objects by providing a second air curtain at the outlet end of low particle count air perpendicular to the direction of transport defining a cooling zone following the sterilizing zone and through which the objects pass; and maintaining a low particle count in the sterilization zone by providing a low turbulence and low particle count current of air parallel to the direction of transport through the sterilization zone between the inlet and cooling zones.

2. A process according to claim 1, wherein the step of providing a low turbulence current of air comprises branching off a portion of the second air curtain and passing the current of air in counter current to the direction of transport.

3. A process according to claim 2, wherein the step of providing a low turbulence current of air comprises substantially entirely withdrawing the current of air from the sterilizing zone at the inlet zone.

4. A process according to claim 1, wherein the current of air is provided at a velocity of from 0.2 to 0.7 m/sec.

5. An apparatus for the continuous sterilization of heat resistant objects; comprising: radiation heating means defining a sterilizing zone having an inlet end and an outlet end; means for continuously transporting objects through the sterilizing zone from the inlet end to the outlet end; means for effecting a first air curtain at said inlet end of low particle count air perpendicular to the direction of transport to define an inlet zone through which the objects are continuously transported; cooling means for effecting a second air curtain at said outlet end of low particle count air perpendicular to the direction of transport to define a cooling zone through which the objects are continuously transported; and means for maintaining a low particle count in the sterilization zone comprising means for effecting a low turbulence and low particle count current of air parallel to the direction of transport through the sterilization zone between the inlet and cooling zones.

6. An apparatus according to claim 5, wherein the means for effecting the current of air comprises means for branching off a portion of the second air curtain to direct the current of air in counter current to the direction of transport.

7. An apparatus according to claim 6, further comprising means for substantially entirely withdrawing the current of air from the sterilizing zone at the inlet zone.

8. An apparatus according to claim 5, wherein the means for transporting comprises an endless conveyor belt, and further comprising an inlet gate at the inlet and comprising an air supply box connected to the radiation heating means for variable adjustment of height above the conveyor belt with a blower connected thereto and an air withdrawal box connected below the conveyor belt with a blower connected thereto.

9. An apparatus according to claim 5, further comprising means for effecting a third air curtain of low particle count air perpendicular to the direction of transport to define an outlet zone following the cooling zone and further comprising adjustable slit shutters disposed between the outlet end and the cooling zone and the cooling zone and the outlet zone.

* * * * *